United States Patent
Frigaard et al.

(10) Patent No.: US 7,345,607 B1
(45) Date of Patent: Mar. 18, 2008

(54) IMPLANTABLE MEDICAL DEVICE WITH ADJUSTABLE SIGMA-DELTA ANALOG-TO-DIGITAL CONVERSION CLOCK RATE

(75) Inventors: Mark A. Frigaard, New Brighton, MN (US); Michael W. Heinks, New Brighton, MN (US); Joel A. Anderson, Brooklyn Park, MN (US); Robert H. Mehregan, East Bethel, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 11/536,942

(22) Filed: Sep. 29, 2006

(51) Int. Cl.
*H03M 3/00* (2006.01)
(52) U.S. Cl. .................................... 341/143
(58) Field of Classification Search ............... 341/143, 341/155; 607/4, 5, 9, 16
See application file for complete search history.

(56) References Cited

U.S. PATENT DOCUMENTS 6,389,315 B1 * 5/2002 Schu et al. ................... 607/16
6,556,859 B1 * 4/2003 Wohlgemuth et al. ...... 600/509

* cited by examiner

*Primary Examiner*—Brian Young
(74) *Attorney, Agent, or Firm*—Daniel G. Chapik; Stephen W. Bauer

(57) ABSTRACT

An implantable medical device, such as a pacemaker or implantable cardioverter defibrillator, uses digital signal processing channels to process sensed time varying signals representing cardiac activity. Each digital signal processing channels includes a sigma-Delta analog-to-digital converter. The clock rate of each sigma-delta analog-to-digital converter is controlled as a function of a signal detection threshold for its respective digital signal processing channel. For higher threshold levels, a reduced clock rate for the sigma-delta analog-to-digital converter results in reduced power consumption and longer battery life.

28 Claims, 2 Drawing Sheets

IMPLANTABLE MEDICAL DEVICE WITH ADJUSTABLE SIGMA-DELTA ANALOG-TO-DIGITAL CONVERSION CLOCK RATE

BACKGROUND OF THE INVENTION

This invention relates to implantable medical devices. In particular, it relates to implantable medical devices having signal processing channels using sigma-delta analog-to-digital converters.

Implantable medical devices (IMD's) are used for a variety of monitoring and therapy delivery purposes. Many IMD's sense physiologic signals and provide outputs, either in the form of delivered therapy or in the form of monitored physiologic activity. For example, pacemakers and implantable cardioverter defibrillators (ICD) include electrodes (and in some cases other sensors) to sense cardiac activity. The sensed signals representing cardiac activity are processed in signal processing channels, and are used in the detection of cardiac arrhythmias and other conditions that require the delivery of therapy. The types of therapy that can be delivered include pacing pulses and cardioversion/defibrillation shocks delivered to the heart.

The signal processing of physiological signals, such as signals representing cardiac activity, has generally been performed by analog circuitry. Digital signal processing offers potential benefits over analog circuitry currently used in IMDs, but also poses challenges to implementation in IMDs. To achieve digital signal processing in an IMD, analog physiologic signals must be converted to digital form, through the use of analog-to-digital converters. One of the challenges presented in implementing digital signal processing channels in IMDs has been the amount of electrical energy consumed by the analog to digital conversion process. IMDs typically use batteries contained within the IMD housing as a sole source of electrical energy. The rate at which electrical energy from the battery is used affects battery life, and therefore the usable life of the IMD.

BRIEF SUMMARY OF THE INVENTION

An IMD with digital signal processing channels uses a sigma-delta analog-to-digital converter in each channel to convert incoming signals. A master control selects a conversion clock rate for each sigma-delta converter based upon a signal threshold for the channel in which the sigma-delta converter operates.

The quantization noise of a sigma-delta ADC is a function of its conversion clock rate (which affects the oversampling ratio of the sigma-delta ADC). The power consumption of a sigma-delta ADC is also a function of its conversion clock rate/oversampling ratio. For a given threshold-to-noise ratio, those signal processing channels where signal thresholds are higher can accept a higher quantization noise level, and therefore the master controller can set the conversion clock rate for the sigma-delta ADC at a lower rate. This reduces power consumption by the sigma-delta ADC. As a result, IMD longevity can be increased for patients with higher sensing thresholds by operating each sigma-delta ADC and its associated signal processing channel at a conversion clock rate based upon the signal threshold for that channel.

DETAILED DESCRIPTION

Figure 1:
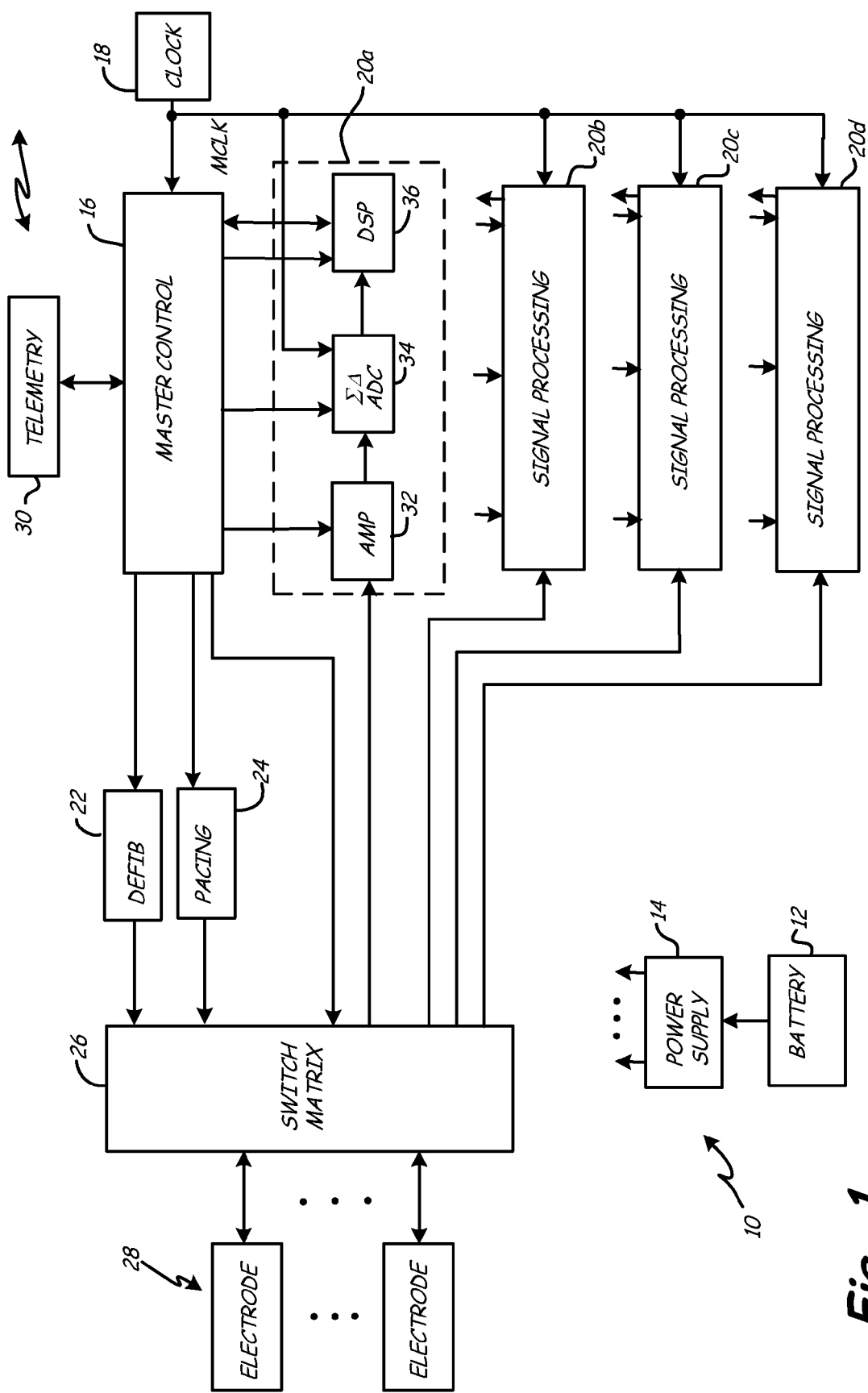
FIG. 1 is a block diagram of an implantable cardioverter defibrillator (ICD) including digital signal processing channels each having a sigma-delta analog-to-digital converter (ADC) operating at a conversion clock rate that is a function of a signal threshold value for that channel.

FIG. 1 is a block diagram of implantable cardioverter defibrillator (ICD) 10, which includes battery 12, power supply 14, master control 16, clock circuitry 18, signal processing channels 20a-20d, defibrillation circuitry 22, pacing circuitry 24, switch matrix 26, electrodes 28, and telemetry interface 30. Each of the signal processing channels 20a-20d is a digital signal processing channel that includes preamplifier 32, sigma-delta analog-to-digital converter (ADC) 34, and digital signal processor (DSP) 36.

Battery 12 and power supply 14 provide all of the electrical energy used by ICD 10 to perform sensing, therapy delivery, and communication with other devices. This includes supply voltages required to operate the electronic circuitry of ICD 10, and the energy required by pacing circuitry 24 to deliver pacing pulses and the voltages required by defibrillation circuitry 22 to provide cardioversion and defibrillation shocks.

Master control 16 controls the overall operation of ICD 10. It provides control inputs to each of the signal processing channels 20a-20d, determines the appropriate therapy based upon the outputs of signal processing channels 20a-20d together with stored detection criteria and therapy delivery programs, provides control signals to defibrillation circuitry 22 and pacing circuitry 24, and communicates with external devices through telemetry interface 30. Master control 16 can provide information regarding the status and operation of ICD 10 through telemetry interface 30 to an external device such as a programmer or a monitor, and may also receive downloads of information, including control settings, from an external programmer through telemetry interface 30.

Master control 16 may include, for example, a microcontroller, memory for data storage, memory for storing software and firmware, and memory for storing control settings and other information that may be provided via telemetry interface 30.

Clock circuitry 18 provides master clock (MCLK) signals to master control 16, as well as to signal processing channels 20a-20d. In the embodiment shown in FIG. 1, each signal processing channel 20a-20d derives from master clock MCLK the necessary clock signals to operate circuitry within that channel, including sigma-delta ADC 34.

Electrodes 28 may be carried by leads that extend from the housing of ICD 10 to locations in or near the heart. For example, electrodes 28 may be carried by leads that extend into the right atrium, into the right ventricle, and through the coronary sinus into a coronary vein adjacent the left ventricle. In addition, electrodes 28 can also be carried by the housing of ICD 10.

Electrodes 28 are used to sense electrical activity of the heart, as well as to deliver pacing pulses or cardioversion/defibrillation shocks to the heart. Switch matrix 26 connects different electrodes to different components of ICD 10 depending on the sensing or therapy delivery function required.

Defibrillator circuitry 22 delivers high voltage shocks to the heart under the control of master control 16. The shocks are provided from defibrillation circuitry 22 through switch matrix 26 to selected electrodes 28. Similarly, master control 16 provides control signals to pacing circuitry 24, to cause pacing pulses to be delivered through switch matrix 26 to selected electrodes 28 in order to deliver pacing therapy.

Although in the embodiment of ICD 10 shown in FIG. 1 electrodes 28 are used to provide signals representing cardiac activity, other forms of sensors may also be used to provide sense signals that are processed by one or more of signal processing channels 20a-20d.

Each of signal processing channels 20a-20d comprises a digital signal processing channel for receiving input signals, converting those signals to digital form, processing those digital signals, and delivering the results of the signal processing to master control 16. The use of digital signal processing channels 20a-20d has significant advantages. Because most of the signal processing occurs in the digital rather than the analog realm, the same basic architecture and components can be used to provide a variety of different signal processing features. Changes in the signal processing can be made by changing instructions to master control 16, which in turn controls digital signal processor 36, rather than requiring redesign or replacement of analog components or circuits. In addition, the use of digital signal processing offers the potential of using high density digital integrated circuitry to implement signal processing functions.

As illustrated the input signal received by preamplifier 32 is an analog signal, which must be converted to digital form in order to perform digital signal processing functions. Preamplifier 32 is, in this embodiment, a variable gain preamplifier, although other types of preamplifier circuits may be used in other embodiments. Alternatively, preamplifier 32 could be omitted entirely in embodiments where electrodes 28 and/or switch matrix 26 are adapted to provide appropriate signals directly for conversion to digital form. Master control 16 provides control settings to preamplifier 32 to select the appropriate gain for that particular signal channel.

Sigma-delta ADC 34 receives the output of preamplifier 32 and converts the analog signal at its input to a digital value that is then provided to digital signal processor 36. Sigma-delta ADC 34 also receives the master clock MCLK signal from clock circuitry 18, and a clock rate control signal from master control 16. Based upon the clock rate control signal, sigma-delta ADC 34 divides master clock MCLK to an appropriate conversion clock (CCLK) rate to perform sigma-delta analog-to-digital conversion. Typically, conversion clock CCLK has a number of different phases that are used within sigma-delta ADC 34 in the conversion process.

Sigma-delta ADC 34 can make use of a single stage or multiple stages of integration in the conversion process, and can provide a digital output in a single-bit or a multi-bit form. An advantage of sigma-delta ADC 34 is a relatively low energy consumption in the conversion process.

Both the quantization noise and the power consumption of sigma-delta ADC 34 are a function of the conversion clock (CCLK) rate; reducing the conversion clock rate reduces the oversampling ratio of sigma-delta ADC 34, which increases quantization noise and reduces power consumption. In an implantable medical device such as ICD 10, the input signal thresholds in the different signal processing channels can differ greatly, and each channel operates independently of the others. Each sensing channel will have a threshold-to-noise ratio requirement. If the threshold is higher, a higher quantization noise value is acceptable to achieve the same threshold-to-noise ratio requirement, and thus the conversion clock rate (and oversampling ratio) can be reduced so that less power is consumed.

Master control 16 maintains information regarding the threshold for each signal processing channel 20a-20d. The threshold information may be supplied to master control 16 by a programmer through telemetry interface 30. The threshold levels may be established, for example, during tests that are performed to establish the threshold for each signal level. These tests may be performed in conjunction with a programmer, or may be performed periodically by master control 16 to adjust thresholds as appropriate.

Using the threshold information for each signal processing channel, master control 16 selects the conversion clock rate/oversampling ratio which is appropriate for the sigma-delta ADC 34 in each signal processing channel. The conversion clock rate information is supplied by master control 16 to each sigma-delta ADC 34 to establish the conversion clock rate that will be used.

As an example, with signals representing cardiac activity, signal level detection thresholds may range from about 150 microvolts to about 11 millivolts. When the threshold is very small (such as a 150 microvolt threshold), the quantization noise generated by sigma-delta ADC 34 is a much larger concern than when the sensing threshold is very large (such as 11 millivolts). As a result, a faster conversion clock rate/higher oversampling ratio may be needed for the very low signal detection threshold, as compared to the very high signal detection threshold. With a high threshold, it is possible to use a much slower conversion clock/lower oversampling ratio, since the threshold level is much higher than the level of quantization noise, even at a slower clock rate/lower oversampling ratio.

By storing a threshold value for each signal processing channel 20a-20d, master control 16 can tailor the conversion clock rate of each signal processing channel 20a-20d to the particular type of input signal being processed. Where a high conversion clock rate is not required, a lower conversion clock rate is used, resulting in lower power consumption.

Figure 2:
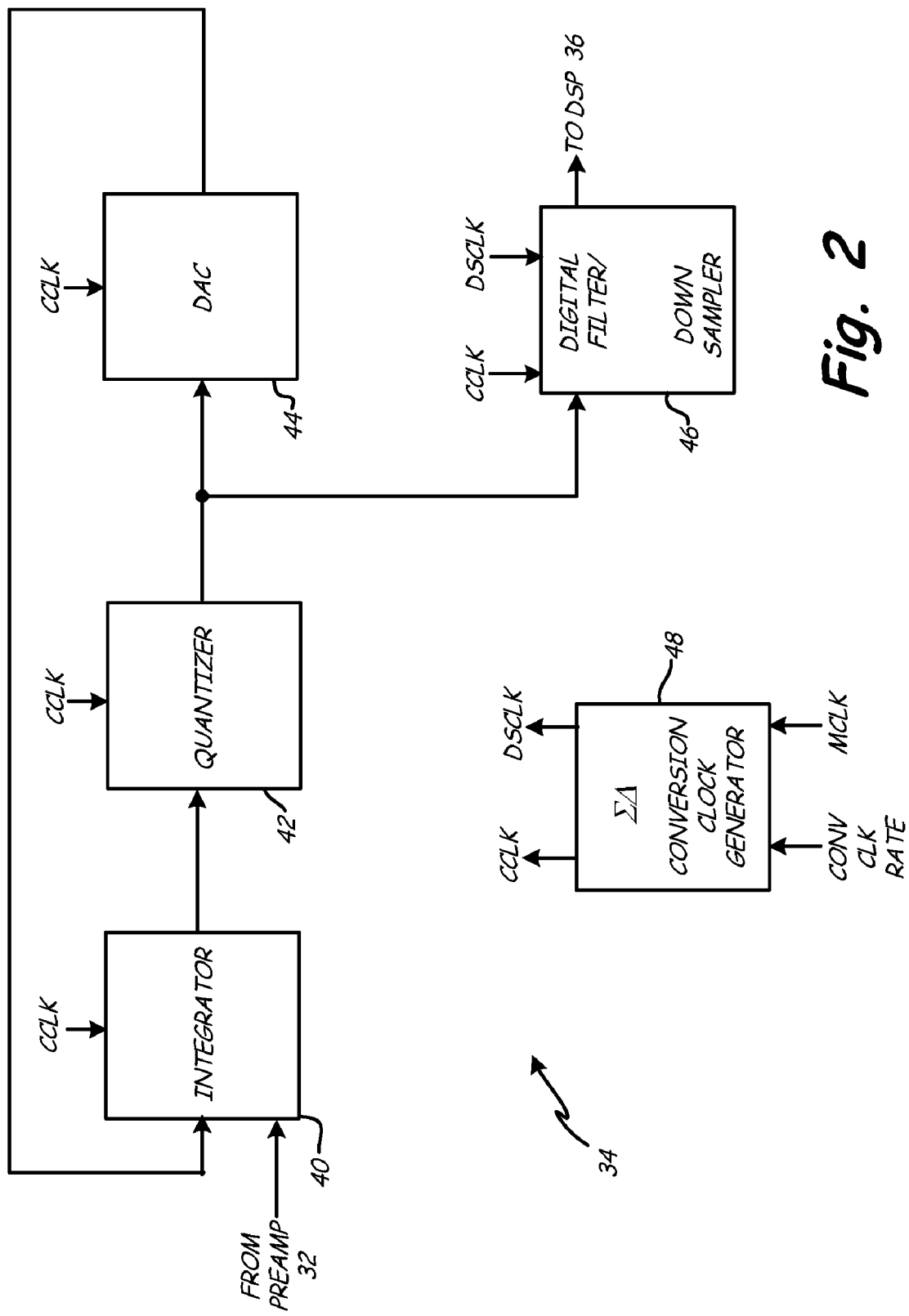
FIG. 2 is a block diagram of one embodiment of a sigma-delta ADC for use in the ICD of FIG. 1.

FIG. 2 shows an example of one embodiment of sigma-delta ADC 34. In this embodiment, sigma-delta ADC 34 is a single stage integration converter that includes integrator 40, quantizer 42, digital-to-analog converter (DAC) 44, digital filter/down sampler 46, and conversion clock generator 48.

Sigma-Delta clock generator 48 receives master clock MCLK and the conversion clock rate command from master control 16, and produces all of the necessary phases of conversion clock CCLK and down sample clock DSCLK. As shown in FIG. 2, integrator 40, quantizer 42, DAC 44, and digital filter/down sampler 46 all operate in response to the conversion clock CCLK, which is based upon master clock MCLK from clock circuitry 18 and the conversion clock rate provided to sigma-Delta ADC 34 by master control 16. In other embodiments, integrator 40 may be operated without the need for a CCLK input.

The analog input signal, as amplified by preamplifier 32, is received at one input of integrator 40, and the output of digital-to-analog converter 44 is received and the other input. Integrator 40 compares the difference between the output of DAC 44 and the input signal from preamplifier 32 and integrates that difference.

Quantizer 42 checks the output of integrator 40 relative to a reference value, and changes its digital output as a function of the integrator output. A change in the output of quantizer 42 results in a change in the output of DAC 44, which is fed back to integrator 40.

The output of quantizer 42 is also provided to digital filter/down sampler 46, which down samples the quantizer output and provides a filtered output to digital signal processor 36. The purpose of down sampling is to provide DSP 36 with digital input at a clock rate that is the same, regardless of the conversion clock rate being used by sigma-delta ADC 34.

Accordingly, by individually controlling the conversion clock rate (and thus the oversampling ratio) used by the sigma-delta ADC 34 of each signal processing channel 20a-20d, power consumption for the analog-to-digital conversion process is reduced. The conservation of power increases battery life, which can extend the usable life of the implantable medical device.

Although the present invention has been described with reference to preferred embodiments, workers skilled in the art will recognize that changes may be made in form and detail without departing from the spirit and scope of the invention. For example, although the present invention has been described in the context of a particular type of implantable medical device (ICD 10), it is also applicable to other types of implantable medical devices in which time varying physiological signals may be sensed, converted to digital form, and then processed and used to provide data monitoring, control of delivery of therapy, or other functions.

What is claimed is:

1. An implantable medical device comprising:
   a plurality of sensing devices for providing a plurality of time-varying physiologic signals;
   a plurality of digital signal processing channels for processing the time-varying physiologic signals, each channel including a sigma-delta analog-to-digital converter; and
   a master control for controlling a conversion clock rate of the sigma-delta converter of each channel as a function of a signal threshold for that channel.

2. The implantable medical device of claim 1, wherein the physiologic signals are representative of cardiac activity.

3. The implantable medical device of claim 2, wherein the plurality of sensing devices comprise electrodes.

4. The implantable medical device of claim 3, wherein the electrodes are carried on leads extending into or near a patient's heart.

5. The implantable medical device of claim 1, and further comprising:
   a therapy delivery device controlled by the master control as a function of outputs of the digital signal processing channels.

6. The implantable medical device of claim 1, and further comprising:
   a telemetry interface connected to the main control.

7. The implantable medical device of claim 6, wherein the master control receives signal threshold information for each channel from the telemetry interface.

8. The implantable medical device of claim 1, wherein the master control provides conversion clock rate information to each sigma-delta analog-to-digital converter.

9. The implantable medical device of claim 1, wherein each channel includes:
   a preamplifier that amplifies one of the physiologic signals and supplies the amplified physiologic signal to the sigma-delta analog-to-digital converter; and
   a digital signal processor that receives a digital output of the sigma-delta analog-to-digital converter and supplies a processor output to the master control.

10. The implantable medical device of claim 9, wherein the preamplifier has a gain that is controlled by the master control.

11. The implantable medical device of claim 1, wherein the sigma-delta analog-to-digital converter includes an integrator, a quantizer, a digital-to-analog converter, and a digital filter, wherein the integrator integrates a difference between an input signal based upon one of the physiologic signals and an analog output of the digital-to-analog converter, the quantizer compares an output of the integrator and a reference value to produce a digital value, the digital-to-analog converter converts the digital value to the analog output, and the digital filter produces a digital converter output based upon the digital value.

12. The implantable medical device of claim 11, wherein the quantizer, the digital-to-analog converter and the digital filter receive clock signals based upon the conversion clock rate.

13. The implantable medical device of claim 12, wherein the digital filter downsamples the digital value to produce the digital converter output at a constant rate irrespective of the conversion clock rate.

14. An implantable medical device comprising:
   a sensor for providing a time-varying physiologic signal;
   a sigma-delta analog-to-digital converter for converting the physiologic signal to a digital signal at a conversion clock rate;
   a digital signal processor for processing the digital signal; and
   a master control for controlling a conversion clock rate of the sigma-delta converter as a function of signal threshold information.

15. The implantable medical device of claim 14, wherein the physiologic signal is representative of cardiac activity.

16. The implantable medical device of claim 14, wherein the sensor comprises at least one implantable electrode.

17. The implantable medical device of claim 14, and further comprising:
   a therapy delivery device controlled by the master control as a function of the output of the digital signal processor.

18. The implantable medical device of claim 14, and further comprising:
   a telemetry interface connected to the main control.

19. The implantable medical device of claim 18, wherein the master control receives signal threshold information from the telemetry interface.

20. The implantable medical device of claim 14, wherein the sigma-delta analog-to-digital converter includes an integrator, a quantizer, a digital-to-analog converter, and a digital filter.

21. The implantable medical device of claim 20, wherein the quantizer, the digital-to-analog converter and the digital filter receive clock signals based upon the conversion clock rate.

22. The implantable medical device of claim 21, wherein the digital filter downsamples the digital value.

23. A method of processing a time-varying physiologic input signal in an implantable medical device, the method comprising:
   converting the input signal to a digital signal with a sigma-delta analog-to-digital converting operating at a conversion clock rate that is controlled as a function of a signal threshold for the input signal; and
   digital signal processing the digital signal from the sigma-delta analog-to-digital converter.

24. The method of claim 23, and further comprising:
   preamplifying the input signal prior to converting the input signal to a digital signal.

25. The method of claim 23, and further comprising:
   controlling the conversion clock rate based upon stored signal threshold information.

26. The method of claim 25, and further comprising:
   transmitting the signal threshold information to the implantable medical device by telemetry.

27. The method of claim 23, wherein the input signal is representative of cardiac activity.

28. The method of claim 23, wherein the input signal is derived from at least one implanted electrode.

* * * * *